United States Patent
Bhatt et al.

(10) Patent No.: US 10,489,919 B2
(45) Date of Patent: Nov. 26, 2019

(54) MOTION-BASED IMAGE SEGMENTATION SYSTEMS AND METHODS

(71) Applicant: ACIST MEDICAL SYSTEMS, INC., Eden Prairie, MN (US)

(72) Inventors: Advit Bhatt, Danville, CA (US); Wouter Vlaanderen, Fremont, CA (US); Jung Wook Suh, Palo Alto, CA (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 11 days.

(21) Appl. No.: 15/594,789

(22) Filed: May 15, 2017

(65) Prior Publication Data

US 2017/0330331 A1   Nov. 16, 2017

Related U.S. Application Data

(60) Provisional application No. 62/336,903, filed on May 16, 2016.

(51) Int. Cl.
*G06K 9/00* (2006.01)
*G06T 7/215* (2017.01)
(Continued)

(52) U.S. Cl.
CPC .......... *G06T 7/215* (2017.01); *A61B 5/02007* (2013.01); *A61B 8/12* (2013.01);
(Continued)

(58) Field of Classification Search
CPC ....... A61B 5/02007; A61B 8/12; G06F 19/34; G06K 9/34; G06T 7/174; G06T 7/215;
(Continued)

(56) References Cited

U.S. PATENT DOCUMENTS 3,918,025 A   11/1975   Koshikawa et al.
4,347,443 A   8/1982   Whitney et al.
(Continued)

FOREIGN PATENT DOCUMENTS

CN   101208045 A   6/2008
CN   103025247 A   4/2013
(Continued)

OTHER PUBLICATIONS

Moore et al., "Intravascular Ultrasound Image Processing of Blood-Filled or Blood-Displaced Lumens," U.S. Appl. No. 15/704,710, filed Sep. 14, 2017, 49 pages.
(Continued)

*Primary Examiner* — Tom Y Lu
(74) *Attorney, Agent, or Firm* — Fredrikson & Byron, P.A.

(57) ABSTRACT

Methods and systems are disclosed for segmenting an image. First and second frames of image data are generated at different times. A first portion of the first frame is compared to image data of the second frame, and a second portion of the second frame is selected based on the comparison. A displacement vector between the first portion and the second portion is calculated, where the displacement vector represents relative movement over time between the image data represented by the first portion and the image data represented by the second portion. An image is output with an indicator, and the location of the indicator on the image is determined by using the calculated displacement vector. The indicator can serve to distinguish between items in an imaging view.

20 Claims, 9 Drawing Sheets

(51) Int. Cl.

| | | |
|---|---|---|
| *G06T 7/174* | (2017.01) | |
| *A61B 5/02* | (2006.01) | |
| *A61B 8/12* | (2006.01) | |
| *G06F 19/00* | (2018.01) | |
| *G06K 9/34* | (2006.01) | |
| *G06T 7/223* | (2017.01) | |

(52) U.S. Cl.
CPC .............. *G06F 19/34* (2013.01); *G06K 9/34* (2013.01); *G06T 7/174* (2017.01); *G06T 7/223* (2017.01); *G06T 2207/10132* (2013.01); *G06T 2207/20021* (2013.01); *G06T 2207/30101* (2013.01)

(58) Field of Classification Search
CPC . G06T 2207/10132; G06T 2207/20021; G06T 2207/30101; G06T 7/223
See application file for complete search history.

(56) References Cited

U.S. PATENT DOCUMENTS

| | | | |
|---|---|---|---|
| 4,850,363 | A | 7/1989 | Yanagawa et al. |
| 4,860,758 | A | 8/1989 | Yanagawa et al. |
| 4,949,310 | A | 8/1990 | Smith et al. |
| 5,070,734 | A | 12/1991 | Kawabuchi et al. |
| 5,070,735 | A | 12/1991 | Reichert et al. |
| 5,131,396 | A | 7/1992 | Ishiguro et al. |
| 5,183,048 | A | 2/1993 | Eberle et al. |
| 5,203,338 | A | 4/1993 | Jang et al. |
| 5,363,849 | A | 11/1994 | Suorsa et al. |
| 5,396,285 | A | 3/1995 | Hedberg et al. |
| 5,462,057 | A | 10/1995 | Hunt et al. |
| 5,531,679 | A | 7/1996 | Schulman et al. |
| 5,690,115 | A | 11/1997 | Feldman et al. |
| 5,741,552 | A | 4/1998 | Takayama et al. |
| 5,833,615 | A | 11/1998 | Wu et al. |
| 5,848,969 | A | 12/1998 | Panescu et al. |
| 5,876,343 | A | 3/1999 | Teo et al. |
| 5,921,931 | A | 7/1999 | O'Donnell et al. |
| 6,015,385 | A | 1/2000 | Finger et al. |
| 6,036,650 | A | 3/2000 | Wu et al. |
| 6,132,374 | A | 10/2000 | Hossack et al. |
| 6,139,501 | A | 10/2000 | Roundhill et al. |
| 6,154,572 | A | 11/2000 | Chaddha et al. |
| 6,216,025 | B1 | 4/2001 | Kruger |
| 6,277,075 | B1 | 8/2001 | Torp et al. |
| 6,589,181 | B2 | 7/2003 | Grunwald et al. |
| 6,645,147 | B1 | 11/2003 | Jackson et al. |
| 7,194,294 | B2 | 3/2007 | Panescu et al. |
| 7,691,061 | B2 | 4/2010 | Hirota |
| 7,925,064 | B2 | 4/2011 | Cloutier et al. |
| 2001/0017941 | A1 | 8/2001 | Chaddha |
| 2001/0029336 | A1 | 10/2001 | Teo |
| 2003/0063787 | A1 | 4/2003 | Natanzon et al. |
| 2003/0078497 | A1 | 4/2003 | Ji et al. |
| 2003/0097069 | A1 | 5/2003 | Avinash et al. |
| 2003/0191392 | A1 | 10/2003 | Haldeman |
| 2003/0208123 | A1 | 11/2003 | Panescu |
| 2004/0030250 | A1 | 2/2004 | Stewart |
| 2004/0037164 | A1 | 2/2004 | Garlick et al. |
| 2004/0199047 | A1 | 10/2004 | Taimisto et al. |
| 2005/0119573 | A1 | 6/2005 | Vilenkin et al. |
| 2005/0215897 | A1 | 9/2005 | Sakaguchi et al. |
| 2005/0249391 | A1 | 11/2005 | Kimmel et al. |
| 2006/0253028 | A1 | 11/2006 | Lam et al. |
| 2007/0016068 | A1 | 1/2007 | Grunwald et al. |
| 2007/0036404 | A1 | 2/2007 | Li |
| 2007/0167710 | A1 | 7/2007 | Unal et al. |
| 2007/0201736 | A1 | 8/2007 | Klingensmith et al. |
| 2008/0015569 | A1 | 1/2008 | Saadat et al. |
| 2008/0031498 | A1 | 2/2008 | Corcoran et al. |
| 2008/0200815 | A1 | 8/2008 | Van Der Steen et al. |
| 2008/0234582 | A1 | 9/2008 | Nair et al. |
| 2009/0088830 | A1 | 4/2009 | Mohamed et al. |
| 2009/0284332 | A1 | 11/2009 | Moore et al. |
| 2010/0010344 | A1 | 1/2010 | Ahn et al. |
| 2010/0094127 | A1 | 4/2010 | Xu |
| 2010/0174190 | A1 | 7/2010 | Hancock et al. |
| 2010/0312092 | A1 | 12/2010 | Maurice et al. |
| 2010/0312109 | A1 | 12/2010 | Satoh |
| 2011/0071404 | A1 | 3/2011 | Schmitt et al. |
| 2011/0160586 | A1 | 6/2011 | Li et al. |
| 2011/0257527 | A1 | 10/2011 | Suri |
| 2012/0065511 | A1 | 3/2012 | Jamello, III |
| 2012/0123271 | A1 | 5/2012 | Cai |
| 2012/0170848 | A1 | 7/2012 | Kemp et al. |
| 2013/0109968 | A1 | 5/2013 | Azuma |
| 2013/0303907 | A1 | 11/2013 | Corl |
| 2013/0303910 | A1 | 11/2013 | Hubbard et al. |
| 2013/0317359 | A1 | 11/2013 | Wilson et al. |
| 2014/0099011 | A1 | 4/2014 | Begin |
| 2014/0100440 | A1 | 4/2014 | Cheline et al. |
| 2014/0180078 | A1 | 6/2014 | Nair |
| 2014/0257087 | A1 | 9/2014 | Elbasiony et al. |
| 2014/0268167 | A1 | 9/2014 | Friedman et al. |
| 2014/0276065 | A1 | 9/2014 | He et al. |
| 2014/0316758 | A1 | 10/2014 | Yagi et al. |
| 2014/0350404 | A1 | 11/2014 | Rajguru et al. |
| 2015/0099975 | A1 | 4/2015 | Lam et al. |
| 2015/0141832 | A1 | 5/2015 | Yu et al. |
| 2015/0245776 | A1* | 9/2015 | Hirohata ................ A61B 6/032 600/504 |
| 2015/0356734 | A1* | 12/2015 | Ooga ...................... A61B 6/03 382/131 |
| 2016/0007967 | A1 | 1/2016 | Johnson et al. |
| 2017/0100100 | A1 | 4/2017 | Jamello et al. |
| 2017/0193658 | A1 | 7/2017 | Cardinal et al. |
| 2017/0301089 | A1 | 10/2017 | Lam et al. |
| 2018/0042575 | A1 | 2/2018 | Moore et al. |

FOREIGN PATENT DOCUMENTS

| | | |
|---|---|---|
| EP | 346889 A1 | 12/1989 |
| EP | 851241 A2 | 7/1998 |
| EP | 1387317 A1 | 2/2004 |
| EP | 1988505 A1 | 11/2008 |
| EP | 1609423 B2 | 3/2010 |
| EP | 2488107 A2 | 8/2012 |
| JP | 62221335 A | 9/1987 |
| JP | H09000522 A | 1/1997 |
| JP | 2001333902 A | 12/2001 |
| JP | 2002530143 A | 9/2002 |
| JP | 2004180784 A | 7/2004 |
| JP | 2006014938 A | 1/2006 |
| JP | 2007029520 A | 2/2007 |
| JP | 2007175542 A | 7/2007 |
| JP | 2007229015 A | 9/2007 |
| JP | 2008508970 A | 3/2008 |
| JP | 2008536638 A | 9/2008 |
| JP | 2009545406 A | 12/2009 |
| JP | 4648652 B2 | 3/2011 |
| JP | 2013507227 A | 3/2013 |
| WO | 0101864 A1 | 1/2001 |
| WO | 2006015877 A1 | 2/2006 |
| WO | 2006113857 A1 | 10/2006 |
| WO | 2006122001 A2 | 11/2006 |
| WO | 2007098209 A2 | 8/2007 |
| WO | 2008016992 A1 | 2/2008 |
| WO | 2008110013 A1 | 9/2008 |
| WO | 2011046903 A2 | 4/2011 |
| WO | 2014186268 A1 | 11/2014 |
| WO | 2017062265 A1 | 4/2017 |
| WO | 2017100274 A1 | 6/2017 |

OTHER PUBLICATIONS

Dumane et al., "Use of Frequency Diversity and Nakagami Statistics in Ultrasonic Tissue Characterization," IEEE Transactions on Ultrasonics, Ferroelectrics, and Frequency Control, vol. 48, No. 5, Sep. 2001, pp. 1139-1146.

(56) References Cited

OTHER PUBLICATIONS

Foster, "Transducer Materials and Probe Construction," Ultrasound in Medicine and Biology, vol. 26, Supp. 1, 2000, pp. S2-S5.

Frijlink et al., "High Frequency Harmonic Imaging in Presence of Intravascular Stents," IEEE Ultrasonics Symposium, 2003, pp. 208-211.

Garcia-Garcia et al., "Imaging of coronary atherosclerosis: intravascular ultrasound," European Heart Journal, vol. 3, 2010, pp. 2456-2469.

International Patent Application No. PCT/US2017/032592, International Search Report & Written Opinion dated Jul. 13, 2017, 18 pages.

Waters et al., "Development of a High-Definition Intravascular Ultrasound Imaging System and Catheter," IEEE International Ultrasonics Symposium Proceedings, Oct. 18, 2011, 4 pages.

Seo et al., "Sidelobe Suppression in Ultrasound Imaging Using Dual Apodization with Cross-Correlation," IEEE Transactions on Ultrasonics, Ferroelectrics, and Frequency Control, vol. 55, No. 10, Oct. 2008, pp. 2198-2210.

Shankar et al., "Computer-Aided Classification of Breast Masses in Ultrasonic B-Scans Using a Multiparameter Approach," IEEE Transactions on Ultrasonics, Ferroelectrics, and Frequency Control, vol. 50, No. 8, Aug. 2003, pp. 1002-1009.

Smith et al., "The Maltese Cross Processor: Speckle Reduction for Circular Transducers," Ultrasonic Imaging, vol. 10, No. 3, Jul. 1988, pp. 153-170.

U.S. Appl. No. 61/218,177, titled Vector Domain Image Enhancement for Mechanically Rotating Imaging Catheters, filed Jun. 18, 2009.

Van Der Steen et al., "IVUS Harmonic Imaging," Ultrasound in Medicine and Biology, vol. 26, Supp. 2, 2000, p. A90.

Wang et al., "Optimizing the Beam Pattern of a Forward-Viewing Ring-Annular Ultrasound Array for Intravascular Imaging," IEEE Transactions on Ultrasonics, Ferroelectrics, and Frequency Control, vol. 49, No. 12, Dec. 2002, pp. 1652-1664.

\* cited by examiner

MOTION-BASED IMAGE SEGMENTATION SYSTEMS AND METHODS

PRIORITY CLAIM

This application claims priority to U.S. provisional patent application No. 62/336,903 filed May 16, 2016.

TECHNICAL FIELD

This disclosure relates generally to medical imaging and, more particularly, to the use of motion to discern one or more items in an image.

BACKGROUND

Medical imaging techniques generally can be used to collect data and generate in-vivo visualization of anatomical areas of interest. One such example is intravascular imaging, where vascular structures and lumens may be imaged. For instance, intravascular imaging may be used to produce one or more images of the coronary artery lumen, coronary artery wall morphology, and devices, such as stents, at or near the coronary artery wall. Images generated using medical imaging techniques can be useful for diagnostic purposes, such as identifying diagnostically significant characteristics of a vessel.

In many cases, the ability to identify diagnostically significant characteristics of a vessel necessarily requires that one or more certain items of diagnostic interest are discernable in the generated image. However, items of diagnostic interest in the generated image may be difficult to distinguish from other diagnostically insignificant items in the generated image. This can be especially true where the diagnostically significant and insignificant items have a similar visual texture pattern in the generated image. If a certain item of diagnostic interest cannot be discerned, or is difficult to locate with a high level of confidence, the value of the generated image for medical diagnostic purposes may be constrained.

SUMMARY

This disclosure in general relates to determining differential movement of items over time, and using the differential movement to identify one or more items. In particular, the differential movement of acquired image data representing items can be used to identify such items in the image data, and ultimately produce a diagnostically valuable image from the image data. Certain of the presently disclosed embodiments calculate movement over time of particular portions of image data, and compare the relative movement of the particular portions to determine differential movement between the portions of image data over time. Using the differential movement between portions of image data over time, an image can be displayed with an indicator at a location on the image corresponding to a particular item, or interface between particular items, in the imaging view. In this way, an image is displayed in a manner that conveys to a user where one or more potential items of interest are located in the image. This can be particularly valuable where such items have similar image texture patterns and therefore would otherwise be difficult for a user to visually discern.

One specific, exemplary application of disclosed embodiments is intravascular imaging. Items of an imaged vessel can include blood, plaque, and tissue defining a vessel wall. In many cases, the movement of blood can be different from the movement of plaque and tissue over a period of time. The period of time, as one example, can be a cardiac cycle. Depending on the portion of the cardiac cycle, movement of blood can be greater or less than movement of tissue and plaque, but in any case will generally be different. Consequently, to identifiably distinguish blood from plaque, and thereby identify an interface between the vessel lumen through which blood flows and plaque build-up thereat, embodiments can determine locations where differential movement between image data is beyond a predetermined degree. Embodiments may then use the determined location(s) of the differential movement as a location for displaying an indicator representing an interface between a vessel lumen and plaque in this example.

In one embodiment, first and second frames of image data are generated at different times, such that the image data of the first frame is from a period of time different than that of the image data of the second frame. A first portion of the image data of the first frame is selected and compared to image data of the second frame. Based on this comparison, a portion of the second frame is selected as corresponding to the image data of the first portion of the first frame. A displacement vector is calculated as representing movement between the image data of the first portion and the corresponding image data of the second portion over the period of time. This process can be repeated so as to calculate a number of displacement vectors, each representing movement over time between particular image data of a portion of the first frame and corresponding image data of a portion of the second frame. The calculated displacement vectors can be compared to determine a location where movement of particular image data differs relative to other image data beyond a predetermined degree. This location can then be used as a location for an indicator on a displayed image. In some cases, the indicator can serve to identify different items, or an interface between different items, in an imaging view.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
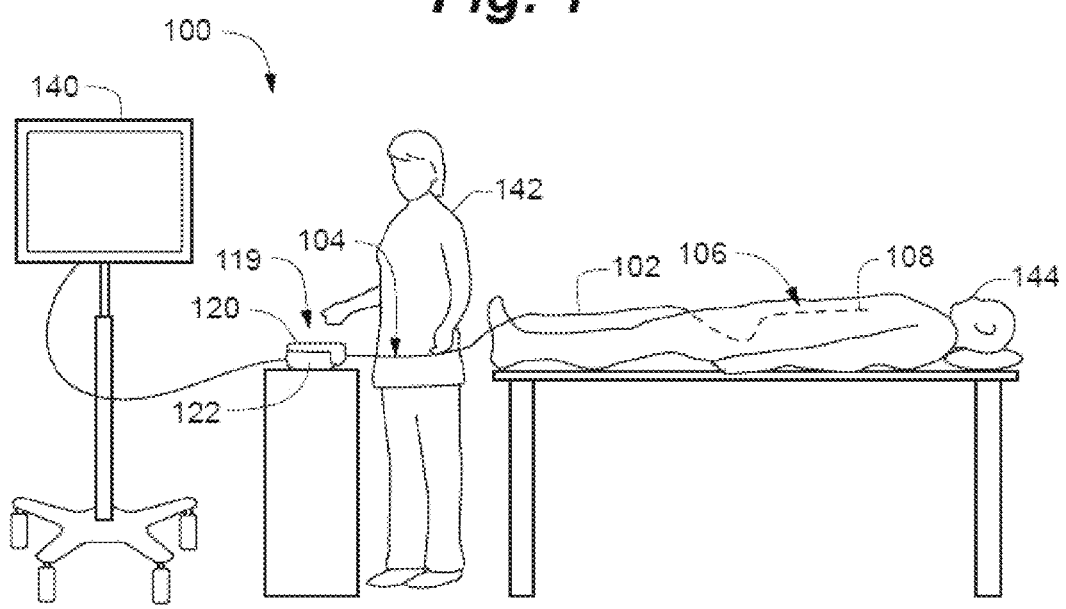
FIG. 1 is an illustrative example of a system configured to perform intravascular imaging.

FIG. 1 illustrates an example of a system 100 that may be configured to perform intravascular imaging. System 100 can include a catheter assembly 102, a translation device 119, and an imaging engine 140. The catheter assembly 102 may include a proximal end 104 and a distal end 106 configured to be inserted into a vessel of a patient 144. In one example, catheter assembly 102 may be inserted into the patient 144 via the femoral artery and guided to an area of interest within the patient 144. The broken lines in FIG. 1 represent portions of catheter assembly 102 within the patient 144.

In some examples, the catheter assembly 102 can include an intravascular imaging device 108 configured to generate imaging data. Intravascular imaging device 108 can be in communication with imaging engine 140. In some embodiments, intravascular imaging device 108 is an ultrasound transducer configured to emit and receive ultrasound energy and generate ultrasound imaging data. In other examples, intravascular imaging device 108 is an optical coherence tomography (OCT) device adapted to emit and receive light and generate OCT data. The image data generated by the imaging device 108 can represent a cross-section of an area of interest within the patient 144 at the location of the imaging device 108. The image data generally will represent a plurality of image items at the cross-sectional location of the imaging device 108, such as, for example, blood, various layers of a vessel of the patient 144, and/or any accumulated matter within the vessel (e.g., plaque at a vessel wall).

The translation device 119 can be configured to translate intravascular imaging device 108 of catheter assembly 102. The translation device 119 may comprise a linear translation system (LTS) 122. The LTS 122 may be mechanically engaged with catheter assembly 102 and configured to translate the catheter assembly 102 a controlled distance within the patient 144 during a translation operation, for example a pullback or push-forward operation. System 100 may comprise a patient interface module (PIM) 120 configured to interface the translation device 119 with the catheter assembly 102. Translating the imaging device 108 can allow for cross-sectional image data to be collected at various longitudinal locations within a vessel of the patient 144.

The imaging engine 140 can be in communication with intravascular imaging device 108 and translation device 119. According to some examples, the imaging engine 140 may comprise at least one programmable processor. In some examples, the imaging engine 140 may comprise a computing machine including one or more processors configured to receive commands from a system user 142 and/or display data acquired from catheter assembly 102 via a user interface. The computing machine may include computer peripherals (e.g., keyboard, mouse, electronic display) to receive inputs from the system user 142 and output system information and/or signals received from catheter assembly 102 (e.g., generated image(s) based on the image data from the imaging device 108). In some examples, the user interface of the computing machine may be a touchscreen display configured to act as both an input device and an output device. In some examples, imaging engine 140 may include memory modules for storing instructions, or software, executable by the one or more processors.

Figure 2:
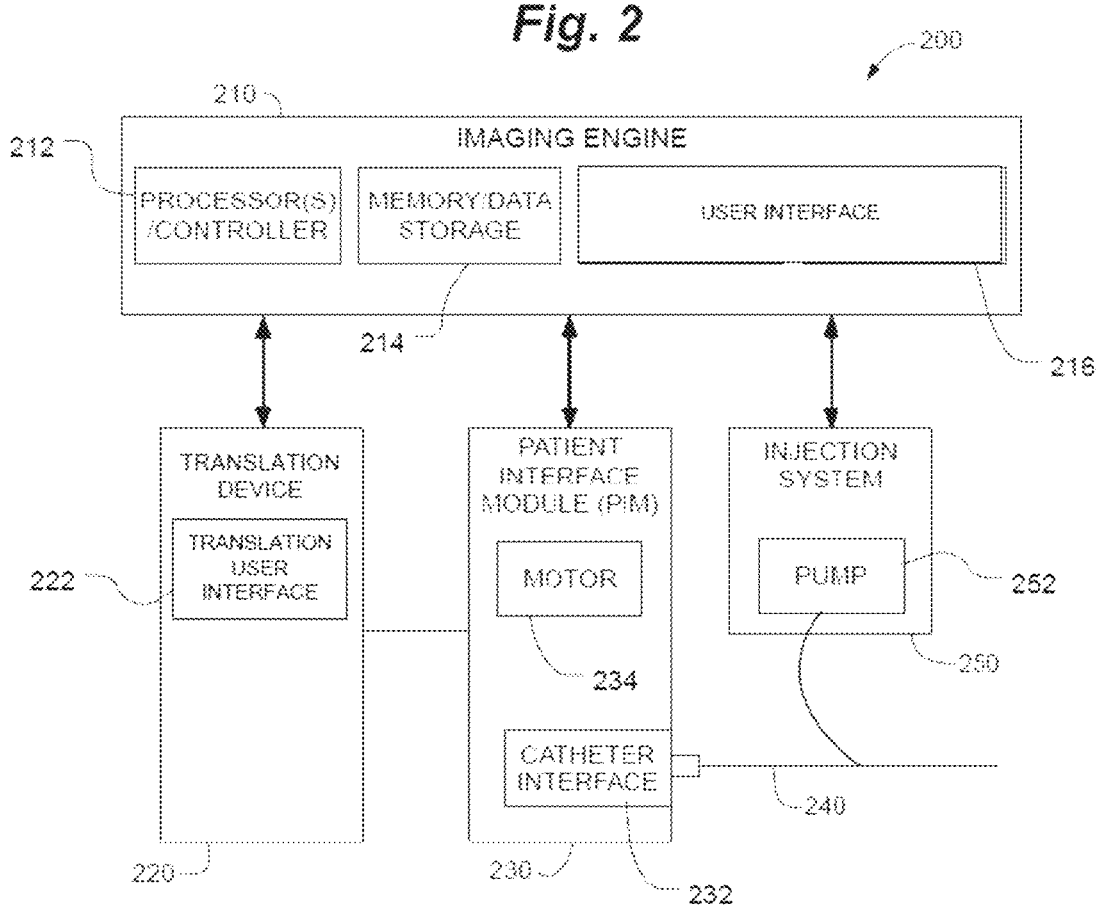
FIG. 2 is a block diagram illustrating an exemplary system configured to perform intravascular imaging.

FIG. 2 is a block diagram illustrating exemplary system 200 adapted to perform intravascular imaging. System 200 can include PIM 230, translation device 220, injection system 250, catheter assembly 240, and imaging engine 210. System 200 can be configured to be used with an OCT and/or an IVUS based intravascular imaging device.

PIM 230 can provide an electromechanical interface between catheter assembly 240 and imaging engine 210. In some embodiments, PIM 230 may provide a catheter interface 232 to secure catheter assembly 240 to system 200. The PIM 230 may include a motor 234 configured to provide mechanical energy to rotate an intravascular imaging device (e.g., ultrasound transducer) of catheter assembly 240. According to various examples, PIM 230 may provide an electrical interface that transmits signals from the intravascular imaging device of catheter assembly 240 and receives return signals.

Translation device 220 can be configured to provide longitudinal translation of catheter assembly 240. Translation device 220 may comprise a Linear Translation System (LTS). The translation device 220 may be configured to mate with PIM 230 and catheter assembly 240 to enable controlled pullback of an intravascular imaging device of catheter assembly 240. According to some examples, translation device 220 may feature a translation user interface 222 which may comprise a translation display configured to display translation data associated with the translation of the intravascular imaging device to a user of system 200. In some embodiments, translation data may include linear distance traversed and/or translation speed. The translation user interface 222 may be configured to receive inputs from a user to control starting/stopping translation, setting translation speed, resetting linear distance traversed to zero, and/or switching to manual mode. In manual mode, a user may freely move the intravascular imaging device of the catheter assembly forward and backward (e.g., distally and proximally within a vessel). In some examples, the translation device 220 may be configured to enable both pullback and push-forward of the intravascular imaging device at a controlled rate. In another example, the translation device 220 may be configured to oscillate, or cycle, the intravascular imaging device by alternately performing pullback and push-forward operations. In some examples, translation device 220 may include a position sensor configured to measure a distance of a translation operation.

The injection system 250 can be configured to deliver fluid into a vessel of a patient via catheter assembly 240. Although, in some embodiments the system 200 may not include the injection system 250. Injection system 250, when present in the system 200, may comprise an injector pump 252 configured to deliver one or more fluids (e.g., contrast or saline) into the patient. In some examples, the injector pump 252 may be automated, in electrical communication with, and controlled by imaging engine 210. According to some examples, injector pump 252 may comprise a manual pump (e.g., syringe injection) configured to allow a user to manually deliver one or more fluids into the patient. As is discussed elsewhere herein, the injection system 250 may be in fluid communication with an intravascular blood displacement fluid port, which may be associated with catheter assembly 240, such that fluid from the injection system 250 is delivered into a patient's vasculature via the intravascular blood displacement fluid port. As can be appreciated, the injection system 250 may be configured to deliver any number of fluids and any quantity of fluid as appropriate for a specific application of system 200. In some examples, the quantity of blood displacement fluid may comprise a contrast media or saline.

The imaging engine 210, in the illustrated example, includes one or more programmable processors 212, memory/data storage component 214 which can be in communication with the one or more programmable processors 212, and a user interface 216 which can be in communication with the one or more programmable processors 212 and/or the memory/storage component 214. The imaging engine 210 can itself be in communication with the translation device 220, PIM 230, and/or injection system 250 (when present). The user interface 216 can include a display for outputting an image generated based on image data acquired by the catheter assembly 240 (e.g., an ultrasound transducer of the catheter assembly). Before the image is output on the display of the user interface 216, image data acquired by the catheter assembly 240 can undergo one or more processing techniques at the imaging engine 210. For instance, the memory/data storage component 214 can include instructions, or software, for performing one or more processing techniques and the one or more processors 212 may execute the processing techniques based on the instructions.

Figure 3:
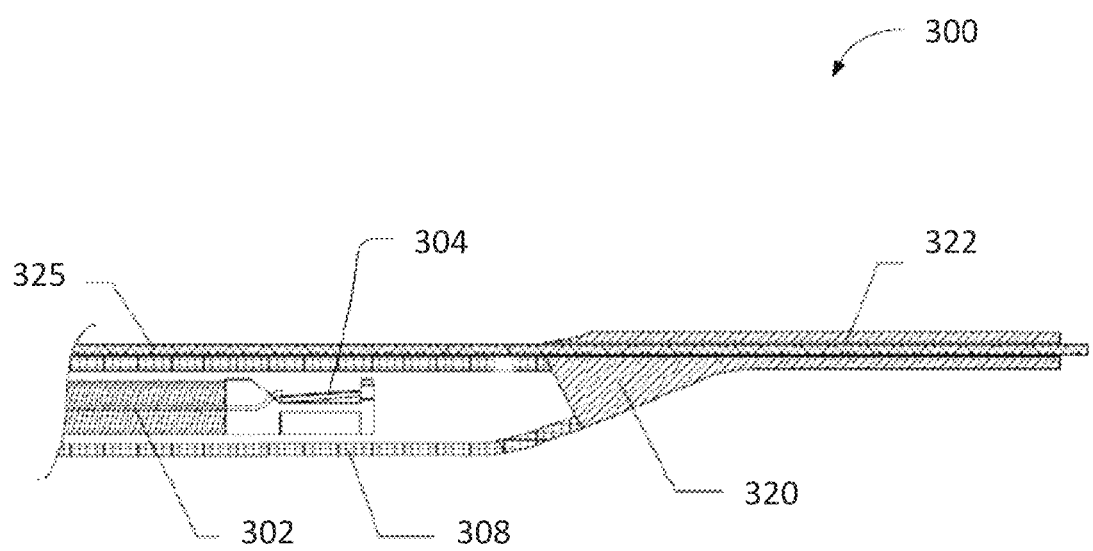
FIG. 3 is a side cross-sectional view of an embodiment of a portion of a catheter assembly.

FIG. 3 shows an exemplary side cross-sectional view of an embodiment of a distal portion of a catheter assembly 300, which can be used in the systems described previously with respect to FIGS. 1 and 2. The catheter assembly 300 may include a drive cable 302, a sheath 308, and an ultrasound transducer 304. As noted above, the drive cable may be coupled to a PIM to rotate the drive cable 302 within sheath 308. The ultrasound transducer 304 may be coupled to the drive cable such that the rotation and/or translation of the drive cable causes ultrasound transducer 304 to rotate and/or translate within sheath 308. The ultrasound transducer 304 may be configured to emit and receive acoustic energy during rotation and/or translation to generate ultrasound data. In some examples, the catheter assembly 300 may also include an imaging window (not shown) substantially transparent to the frequency of the acoustic energy emitted by the ultrasound transducer. The catheter assembly 300 may also include a distal end 320 forming a guidewire lumen 322 configured to accept a guidewire 325 to guide the catheter assembly 300 into a vessel of a patient and/or translate the catheter assembly 300 within the vessel.

Figure 4:
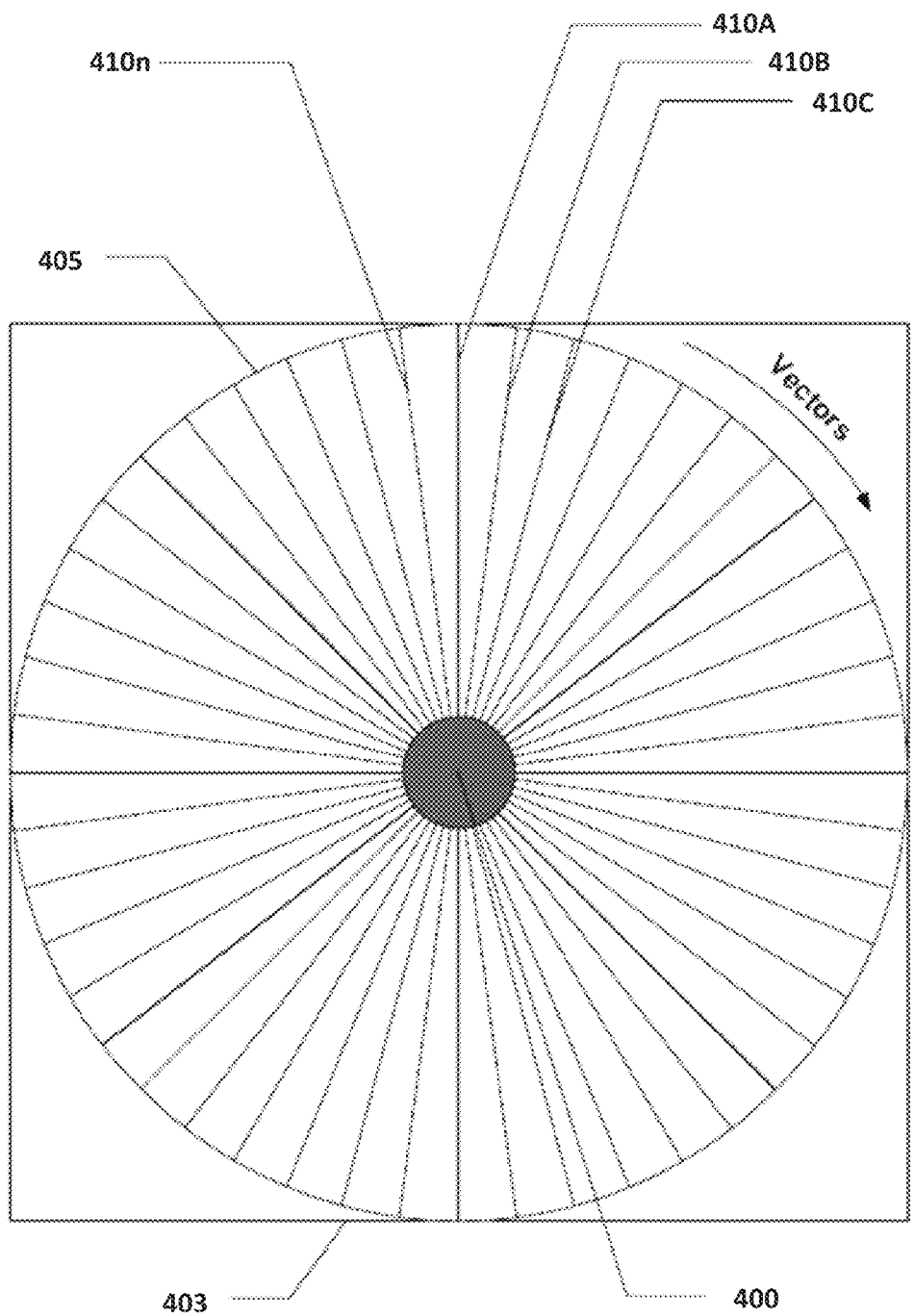
FIG. 4 is an exemplary front view of a catheter including data vectors propagated by a transducer of the catheter.

FIG. 4 illustrates an exemplary front view of propagating ultrasound data vectors of a catheter 400. In this example, the catheter 400 may be a mechanically rotating ultrasound imaging catheter similar to catheters previously described. Likewise, the catheter 400 may be configured to rotate an ultrasound transducer (not shown) relative to a sheath of catheter 400, and the ultrasound transducer may be configured to generate ultrasound data by emitting and receiving acoustic energy. The ultrasound data vectors illustrated in FIG. 4 are indicative of acoustic energy emitted and received by the ultrasound transducer at different rotational positions. More specifically, each data vector is representative of ultrasound data collected by the ultrasound transducer at different rotational positions of the ultrasound transducer.

As shown in FIG. 4, the ultrasound transducer of catheter 400 may generate ultrasound data on a vector-by-vector basis as the transducer is rotated. For example, the ultrasound transducer may initially acquire an ultrasound data vector 410A and continue to acquire vectors 410B through 410*n* as the ultrasound transducer is rotated clockwise. Accordingly, vectors 410A-410*n* can be representative of a full 360 degree rotation of the ultrasound transducer. The transducer can, in some instances, rotate and acquire the data vectors at a constant longitudinal position within the vessel, or, in other instances, rotate and acquire the data vectors simultaneous to longitudinal translation within the vessel. The number of data vectors acquired per rotation may vary depending on the application of the catheter. For instance, in some embodiments, the IVUS catheter is configured to generate between about 500 and about 5000 vectors per rotation. For example, in an embodiment generating 512 vectors per rotation the angle between data vectors may then be characterized as approximately $2\pi/512$ radians or $360/512$ degrees. In an example of a catheter configured to generate 4096 vectors per rotation, the angle between data vectors may be approximately $2\pi/4096$ or $360/4096$ degrees.

FIG. 4 also provides a representation of an image data frame 403 that comprises vectors 410A-410*n*. Data frame 403 includes vectors emitted and received over a first period of time, and thus includes image data generated at the first period of time. In many embodiments, rotation of the transducer can occur at a rate that results in the image data of the data frame 403 being generated at substantially the same time. A field of view 405 of the catheter 400 may be based on the magnitude of the data vectors propagated by the catheter and may vary to suit a specific application. The magnitude of the data vectors may be based on a number of factors, for example, the frequency of the emitted wave and/or the power level of the wave.

The ultrasound transducer of catheter 400 can emit acoustic energy at one or more frequencies. In one example, the ultrasound transducer can emit acoustic energy at a frequency of approximately 60 MHz. In another example, the ultrasound transducer can emit acoustic energy at a frequency of approximately 40 MHz. Image data generated at a low frequency (e.g., equal to or less than 40 Mhz) generally exhibits good contrast but poor spatial resolution, while image data acquired at a high frequency (e.g., greater than 40 MHz, such as 60 MHz) generally exhibits good spatial resolution but poor contrast. Thus, the frequency at which the transducer emits energy and acquires data vectors may vary depending on the particular application. In some examples, the transducer can emit and acquire data vectors at more than one frequency, whether the data vectors alternate in frequency sequentially or non-sequentially during a single rotation of the transducer.

Figure 5:
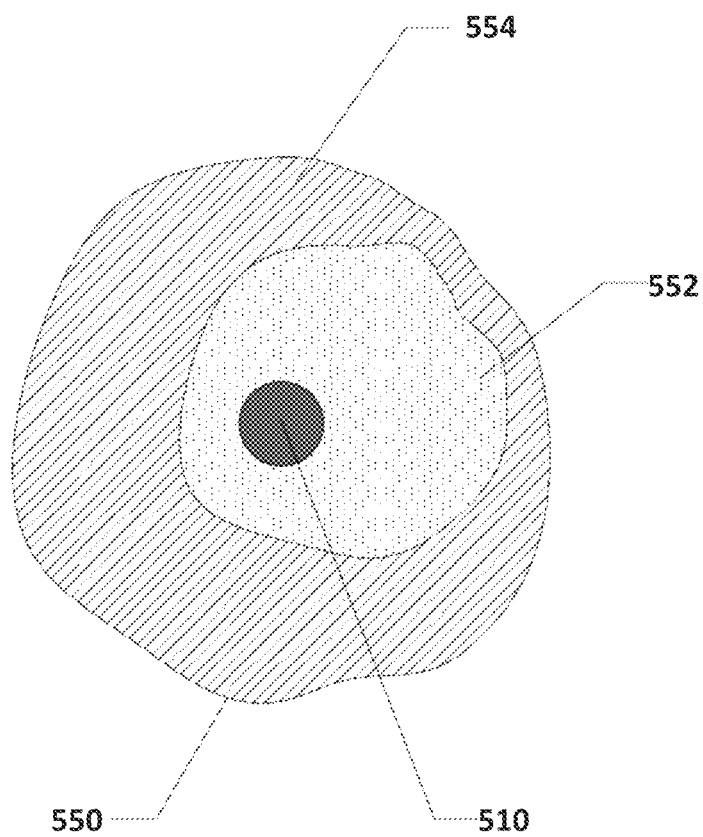
FIG. 5 is an exemplary cross-sectional view of a catheter in a vessel lumen.

FIG. 5 is a cross-sectional view showing a catheter 510 within a vessel 550. As noted above, catheter 510 may be directly guided into the vessel or, in certain examples, be guided into the vessel via a guide wire. Once the catheter 510 is guided to a desired longitudinal location within the vessel 550, the catheter 510 via the imaging device and imaging module thereof (e.g., ultrasound transducer) can emit and receive energy. This can be, in some examples, in the form of a plurality of data vectors acquired during rotation of the imaging module, such as shown in FIG. 4. The catheter 510 can thereby generate cross-sectional image data.

The vessel 550 may be a vessel of a vascular system of a patient including a vessel wall 554 defining a vessel lumen 552 through which blood flows. In addition to blood, the vessel lumen 552 may also include, in various applications, one or more plaque components that have accumulated within the vessel lumen 552 over time, such as at the interface of the vessel wall 554 and the vessel lumen 552. Such plaque components can include, for instance, atherosclerotic plaque such as lipids.

In some instances, the image generated using the image data collected by the catheter 510 (e.g., by the imaging module thereof) can allow a user to visually discern certain structures of the vessel 550 more easily than other structures. For example, in one imaging application the generated image may visually present to a user a relatively identifiable external elastic membrane boundary of the vessel 550. Yet, in the same generated image it may be difficult for a user to visually identify a boundary between the vessel lumen 552 and plaque accumulated within the vessel lumen 552 along the inner surface of the vessel wall 554. This can be a result of the image texture patterns of blood within the lumen 552 and plaque appearing visually similar in the generated image. However, in many applications the interface between blood within the lumen 552 and plaque along an inner surface of the vessel wall 554 is an important item to discern in the generated image for diagnostic purposes.

Exemplary embodiments are described herein for indicating various structures, and/or boundaries between such structures, that may otherwise be difficult to visually discern from a generated image. For instance, the described exemplary embodiments can utilize differential movement of items of a vessel over time to distinguish between, and identify, such structures. One such example includes differential movement over time (e.g., over portions of a cardiac cycle) of blood versus tissue and plaque. By identifying one or more structures, and/or boundaries between such structures, that could otherwise be difficult for a user to visually discern, described embodiments can increase the value of the generated image for medical diagnostic purposes.

Figure 6:
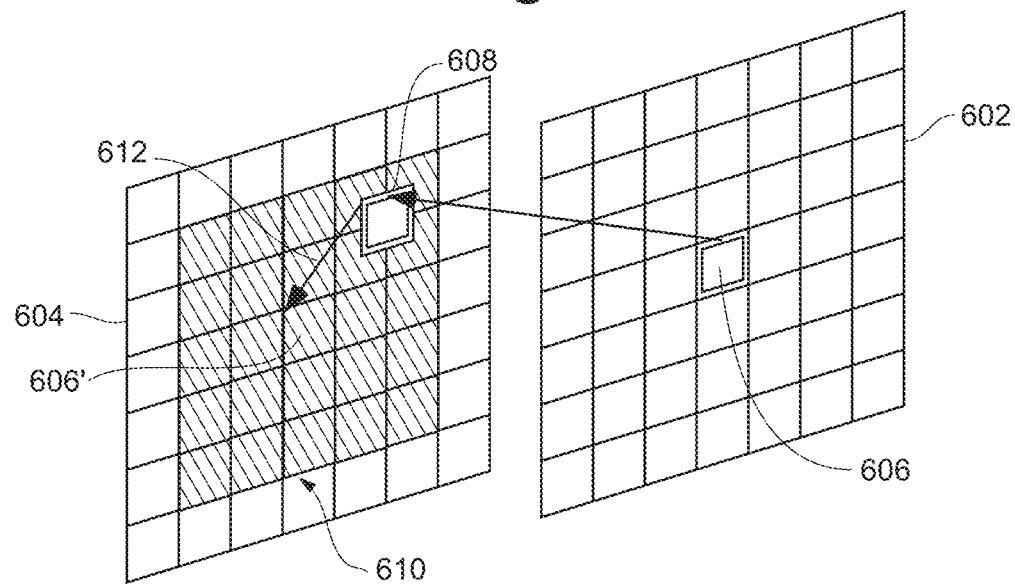
FIG. 6 is an exemplary schematic diagram illustrating comparison of image data frames.

FIG. 6 shows an exemplary schematic diagram illustrating comparison of a first image data frame 602 and a second image data frame 604. Although the comparison is illustrated here to be among two data frames 602, 604 various embodiments can include a similar comparison across any number of data frames (e.g., by using a weighted average). The image data frames 602, 604 can, in some examples, be generated using a system similar to any of those described previously, including an intravascular ultrasound imaging system. In such examples, cross-sectional image data may be collected using a catheter assembly having an intravascular imaging device including an imaging module for emitting and receiving energy also similar to that described previously. The image data frames 602, 604 can each include image data representing a plurality of items in an imaging view of the imaging module (e.g., an ultrasound transducer). In applications where the imaging module is utilized at a location within a vessel, the image data can represent various items within the vessel at the location where the imaging module collected the data. In this application, the image data can represent structures of and within the vessel, including blood, plaque, stent location, various lesions, lumen geometry, and vessel wall structures (e.g. vessel wall layers and interfaces therebetween).

In various examples, the first image data frame 602 and the second image data frame 604 can be generated at first and second times that are different. As one example, the first image data frame 602 can represent image data collected during a first rotation (e.g., full 360 degree rotation) of the imaging module, while the second image data frame 604 can represent image data collected during a second, previous or subsequent rotation (e.g., full 360 degree rotation) of the imaging module. Where the imaging module is deployed within a vessel, the first data frame 602 can be taken at a first time at a first longitudinal location within the vessel, while the second data frame 604 can be taken at a second different time at a second different longitudinal location within the vessel (e.g., as by translating the imaging module within the vessel as described previously). In some cases, the image data frames 602, 604 can be adjacent (e.g., neighboring) frames generated consecutively within the vessel (whether the first data frame 602 is collected previous to or subsequent to the second data frame 604). But, in other cases, the image data frames 602, 604 can be spaced apart by other data frames generated in between the data frames 602, 604 (e.g., spaced apart by one, two, three, five, ten, or more data frames).

The different respective times at which the first and second image data frames 602, 604 are collected can vary, for instance, according to a particular imaging application. As one example where the imaging application is intravascular imaging, the first and second data frames 602, 604 can be generated respectively at different parts of a patient's cardiac cycle (e.g., one frame at the diastole stage and one frame at the systole stage, whether both are of a same single cycle or each is from a different cycle). For instance, the first image data frame 602 can be generated at a first time corresponding to a first part of a patient's cardiac cycle while the second image data frame 604 can be generated at a second time corresponding to a second, different part of the patient's cardiac cycle.

To further facilitate collection of data frames at different parts of the cardiac cycle, a patient's heart rate can be measured and used as an input in the imaging system (e.g., intravascular ultrasound imaging system described previously). The measured heart rate can provide a user with information as to the frequency of the cardiac cycle. In this way, the first time at which the first image data frame 602 is generated and the second different time at which the second image data frame 604 is generated can be determined by using the measured heart rate of the patient. In some instances, the imaging system can use the input of the patient's measured heart rate to automatically control the imaging module to generate image data frames 602, 604 at different parts of the patient's cardiac cycle.

Once image data frames 602, 604 are generated, the first image data frame 602 can be divided up into multiple portions that each have a subset of all image data of the first image data frame 602. In some cases this can be accomplished by first converting the generated image data from a Cartesian coordinate into a Polar coordinate form, but in other cases any form of the image data represented in the image data frames can be used. As shown in the example of FIG. 6, the first image data frame 602 is subdivided up into a number of portions 606 each having a subset of the image data of the first image data frame 602. As shown in the illustrated example here, the first image data frame 602 is subdivided up into a 7×7 series of image blocks. But, in other examples any number of portions 606 can be used (e.g., 2×2, 16×16, etc. series of image blocks) to cover the whole image frame or one or more portions of the image frame. The shape of each the portions 606 can take a variety of shapes (e.g., square, rectangular, circular, elliptical, etc., or even free-form) of various sizes. The number of portions 606 into which the first image data frame 602 can be divided up may depend, for example, on the accuracy desired and/or processing capability available for a particular application.

A particular portion 606 of the first image data frame 602 can be selected and compared to the image data of the second image data frame 604. This comparison can serve to locate image data within the second image data frame 604 that corresponds to the image data represented by the particular portion 606 of the first image data frame 602. This could include, in some cases, determining where the specific item (e.g., vessel structure), or portion of the structure, represented by the particular portion 606 is present within the image data of the second image data frame 604. A variety of techniques can be used to locate image data within the second image data frame 604 that corresponds to the image data represented by the particular portion 606 of the first image data frame 602.

As one example, the selected particular portion 606 of the first image data frame 602 can be compared to image data of the second image data frame 604 to select a portion 608 of the second image data frame 604. The portion 608 of the second image data frame 604 can constitute a subset of all image data of the second image data frame 604. The portion 608 of the second image data frame 604 can be selected based on the comparison by determining that the subset of image data represented by the portion 608 corresponds to the subset of image data represented by the particular portion 606.

In one instance of the comparison in this example, the image data represented by the particular portion 606 of the first image data frame 602 can be compared to image data represented in each of multiple portions of the second image data frame 604. The portion 608 of the second image data frame 604 can then be selected from the multiple portions of the second image data frame 604. In one such instance, the portion 608 can be selected by determining that the portion 608 corresponds to the image data represented by the selected particular portion 606 to a greater degree than image data of any other portion of the second image data frame 604. In some cases, the comparison may include calculating a matching error between the image data of the selected particular portion 606 and the image data of each of the multiple portions of the second image data frame 604. The calculated matching error can be a numerical representation of the similarity of the image data in the compared portions (e.g., a summation of all error calculated between the image data of the compared portions). Where the comparison includes calculating a matching error, the portion 608 can be selected as the portion of the second image data frame 604 that has the lowest matching error with the image data of the particular portion 606.

In some examples, the particular portion 606 can be compared to all image data of the second image data frame 604. In such examples, the multiple portions into which the second image data frame 604 is divided would include all image data of the second image data frame 604. Thus, in these examples the particular portion 606 would be compared, as described previously, to all image data of the second image data frame 604 and the portion 608 accordingly selected from all image data of the second image data frame 604.

In other examples, the particular portion 606 can be compared to only a subset of all image data of the second image data fame 604. In one such example, the particular portion 606 can be compared only to image data of the second image data frame 604 that is within a search window 610 of the second image data frame 604 (e.g., each of the multiple portions of the second image data frame 604 to which the particular portion 606 is compared are within the search window 610). The search window 610 constitutes less than all image data of the second image data frame 604, and thus defines a subset of all image data of the second image data frame 604. When utilized, the size of the search window 610 can vary in different embodiments such as from a size that is just larger than the particular portion 606 (e.g., includes slightly more image data than the particular portion 606) to a size that is just less than the entirety of the second image data frame 604. In the illustrated example, the search window 610 is larger than the particular portion 606 and constitutes a subset of all image data of the second image data frame 604 that excludes image data forming a perimeter of the second image data frame 604. It may be useful to exclude from the comparison with the particular portion 606 image data at one or more locations of the second image data frame 604 which are known to be unlikely to include image data corresponding to the image data of the particular portion 606. In the exemplary application of intravascular imaging where the interface between blood within the vessel lumen and plaque along the vessel wall is to be identified, it may be useful for efficiency purposes in some cases to exclude the perimeter of frame 604 from the comparison to the particular portion 606.

In examples where the search window 610 is utilized, the particular portion 606 of the first image data frame 602 can be compared only to each portion of the second image data frame 604 within the defined search window 610. The portion 608 of the second image data frame 604 can be selected from the search window 610 by determining that the image data represented by the particular portion 606 corresponds to the image data represented by the portion 608 to a greater degree than image data at any other portion of the search window 610. In one instance, this could be determined by the portion 608 having the lowest calculated matching error with the image data represented by the particular portion 606 of all portions within the search window 610.

Although only one frame 602 is shown in the illustrated example, in a further embodiment the second frame 604 can serve as a reference frame for more than one frame 602 in selecting the portion 608. The more than one frame 602 can include one or more frames generated prior to the frame 604 and/or one or more frames generated subsequent to the frame 604. In this embodiment, the particular portion 606 can be selected in each of two or more frames 602, where the particular portion 606 in each of the frames 602 is selected as corresponding to the same image data. A corresponding portion 608 can be selected in a similar manner as that described above for each of the particular portions 606 in each of the frames 602. A weighted average across each of the selected portions 608 in the frame 604 can be used to determine a composite portion in the frame 604, and this composite portion can be used similar to that described further below for the portion 608.

Once the portion 608 of the second image data frame 604 is selected based on the comparison, a displacement vector 612 can be calculated. For illustrative convenience purposes in showing the displacement vector 612, the location of the image data represented by the portion 606 is shown as simulated onto the second image data frame 604 as portion 606'.

The displacement vector 612 can represent relative movement between the image data represented in portions 606 and 608. Where the first and second frames 602 and 604 are generated at different times, the displacement vector 612 can represent movement between the image data represented in portions 606 and 608 over the period of time between generation of the image data frames 602 and 604. Since the portion 608 may be selected as encompassing image data corresponding to image data represented by the portion 606, the displacement vector 612 can serve to represent movement of the same item represented by the image data of the portions 606, 608 over this period of time. Specifically, a length of the displacement vector 612 can be used as a measure of the extent of movement of the item over the period of time between the first and second data frames 602, 604. In the described example, the longer the displacement vector, the greater the degree of movement of the object over the period of time. The degree of movement of the object over the period of time can then be used to determine the identity of the object, allowing such object to be indicated in a generated image.

Once the displacement vector 612 is calculated and stored in memory or otherwise noted, some or all of the described techniques can be repeated for any number of other portions of the first image data frame 602, including all portions of the frame 602. In this way, a number of displacement vectors can ultimately be calculated. Each such displacement vector can represent relative movement between the image data in the respective portion of the first image data frame 602 and the corresponding image data in the respective portion of the second image data frame 604 over the period of time between the first and second data frames 602, 604. The length of each such displacement vector can be stored in memory or otherwise noted. As will be described further below, the relative difference in length of the calculated displacement vectors can be used to identify differential movement over the period of time.

Figure 7:
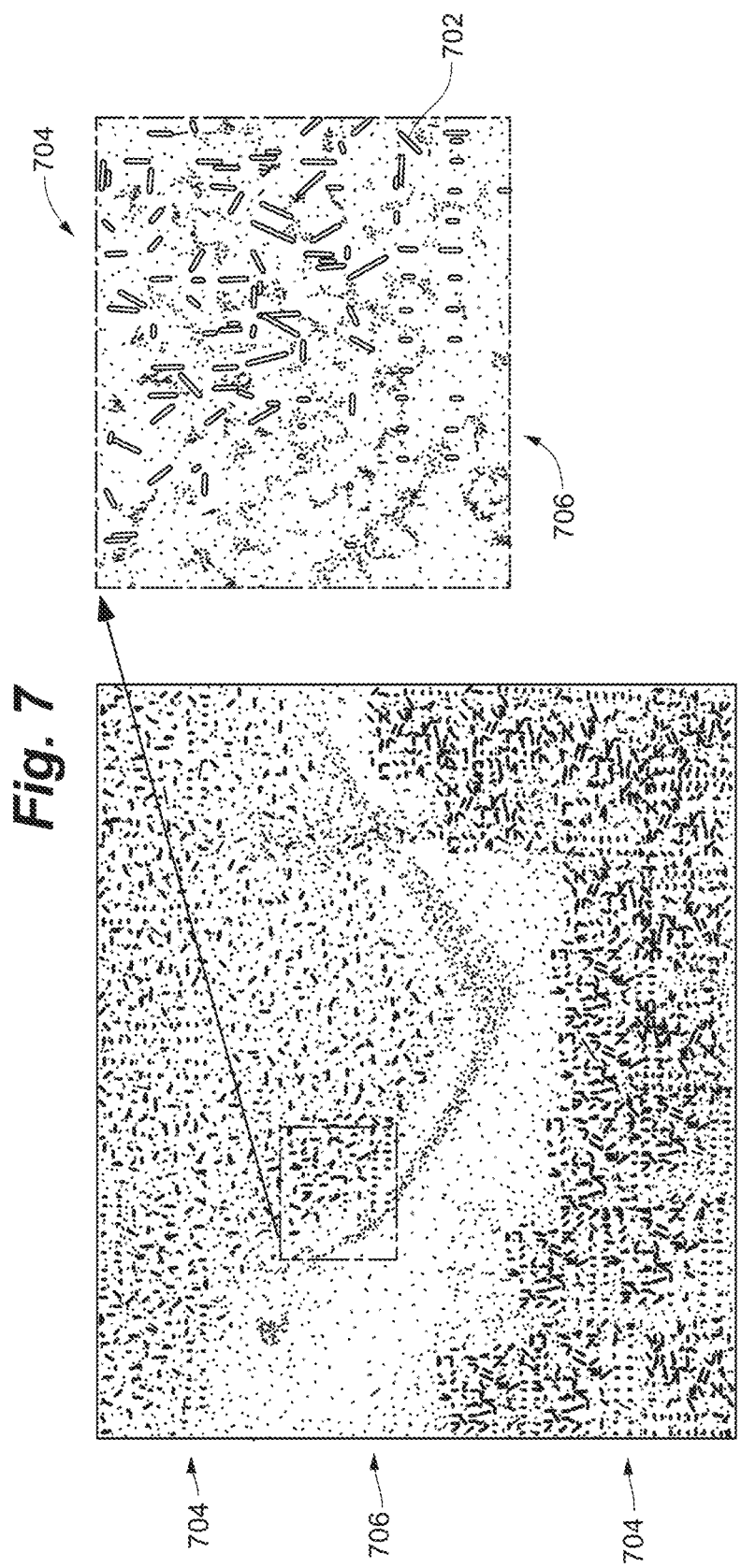
FIG. 7 is an exemplary diagram illustrating a number of displacement vectors calculated from the comparison of FIG. 6.

FIG. 7 shows an exemplary diagram illustrating a number of displacement vectors 702 each calculated using the comparisons described previously with respect to FIG. 6. As noted previously, each displacement vector 702 can serve to represent relative movement over time of corresponding image data of portions of first and second frames (e.g., relative movement of an object in an imaging view over time).

In some embodiments, relative lengths of two or more displacement vectors 702 can be compared, for instance, to distinguish objects in an imaging view. For example, determining that two displacement vectors have differing lengths (or have lengths differing beyond a predetermined degree) can indicate that the image data represented by each moved to differing degrees over the period of time. In some cases, differing degrees of movement of such image data can signify that the respective image data corresponds to different objects in an imaging view. For instance, in an intravascular imaging application, objects in an imaging view can include blood, plaque, and vessel tissue. The movement of blood over time may be distinct from the movement of tissue, and plaque built-up at the tissue, over the same time (e.g., over one or more particular portions of a cardiac cycle). Therefore, in this application, comparing lengths of displacement vectors may allow for a determination as to whether the image data represents blood or rather represents either tissue or plaque.

In the example of FIG. 7, distinct regions having displacement vectors 702 of similar lengths can be seen. In particular, regions 704 are defined by the presence of displacement vectors 702 having a length equal to or greater than a predetermined length, while regions 706 are defined by the presence of displacement vectors 702 having a length less than the predetermined length. These lengths may signify that image data in regions 704 moved to a similar degree over the period of time, and further that image data in regions 706 moved to a similar degree over the period of time different from that of the regions 704. By comparing the relative lengths of multiple displacement vectors 702, it may be determined that regions 704 and 706 correspond to different objects in the imaging view. The location of different objects in the imaging view can be included on an image through the use of an indicator, as will be described further below.

Although the relative lengths of displacement vectors have been discussed herein as useful for distinguishing items in an imaging view based on the extent of movement over time of the item(s), other characteristics of the calculated displacement vectors can be used in addition to, or as an alternative to, the length of the displacement vectors. For example, the direction of the displacement vectors, and therefore the direction in which the image data representing the item has moved over time, can be used to distinguish items in the imaging view. In some instances, using the direction of the displacement vectors can further include using a slope of the displacement vectors in the particular direction to distinguish items in the imaging view. In one example, the indicator can be included on a displayed image at a location on the image that is determined using the length and direction of displacement vectors calculated in the manner described previously.

Figure 8:
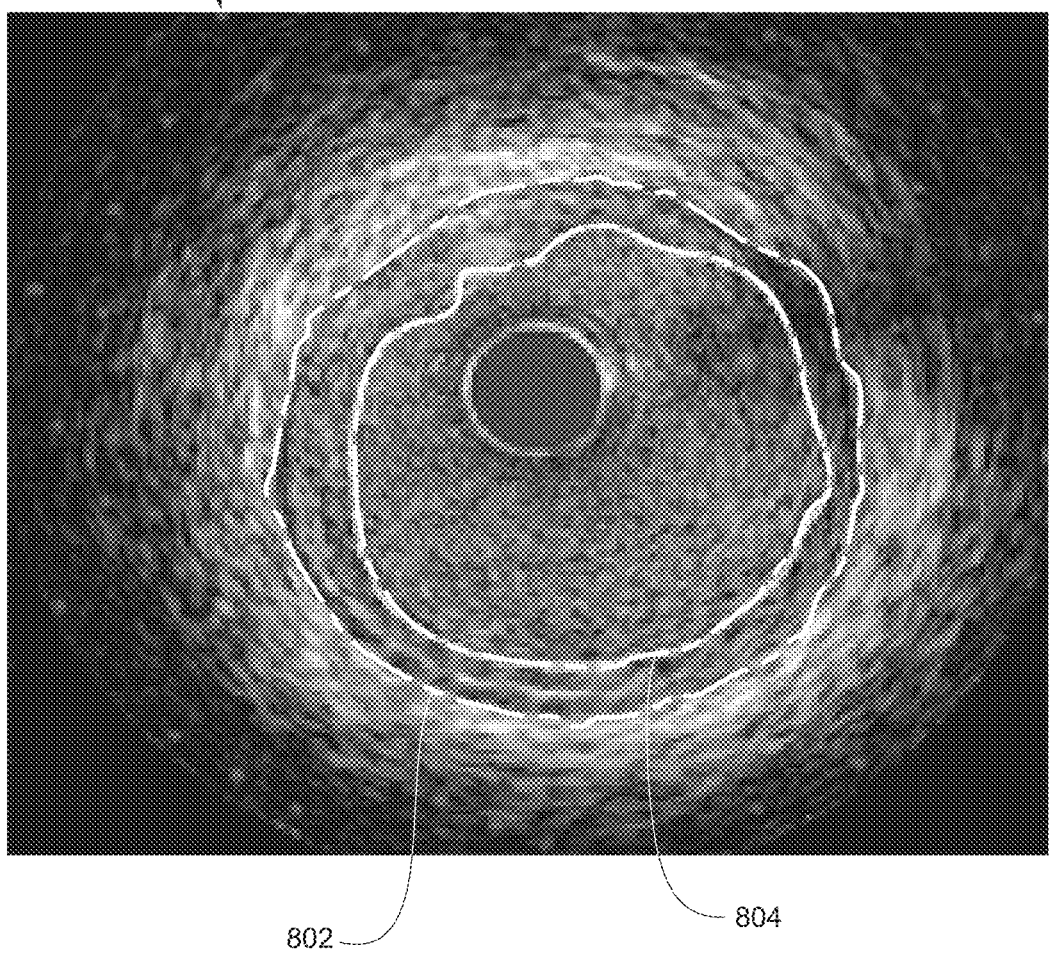
FIG. 8 is an exemplary image output with an indicator.

FIG. 8 shows an exemplary vessel cross-sectional image 800 output with indicators 802 and 804 thereon. In this example, the indicator 802 represents an external elastic membrane boundary of the imaged vessel, while the indicator 804 represents an interface between a vessel lumen and plaque (e.g., accumulated along a vessel wall). One or both of the indictors 802, 804 can be located on the image 800 using the one or more of the calculated displacement vectors. For instance, as described previously, the indicator 804 can be located on the image 800 by comparing two or more of the calculated displacement vectors. A location where the two or more data vectors differ beyond a predetermined degree (e.g., where the lengths of the two or more data vectors differ beyond a predetermined degree) can be used as a location for the indicator 804. This can be repeated over various locations on the image 800 to generate the indicator 804 as shown in FIG. 8. In this way, the indicator 804 is positioned on the output image 800 in one embodiment at a location on the image 800 that is a function of displacement vectors at the location differing in relative length beyond a predetermined degree.

The indicators 802, 804 in the example of FIG. 8 are in the form of solid lines of differing colors, and represent a boundary between items in the imaged vessel. In other examples, one or more indicators can be included on the generated image in various forms. For instance, an indicator could take the form of a shaded region on the image 800 representing a particular item of the vessel at the shaded region. In another instance, an indicator could take the form of an arrow directed to a specific location on the image 800 representing a particular item, or portion of an item (e.g., a portion that is abnormal to the remainder of the item), of the vessel at the location of the arrow.

Figure 9:
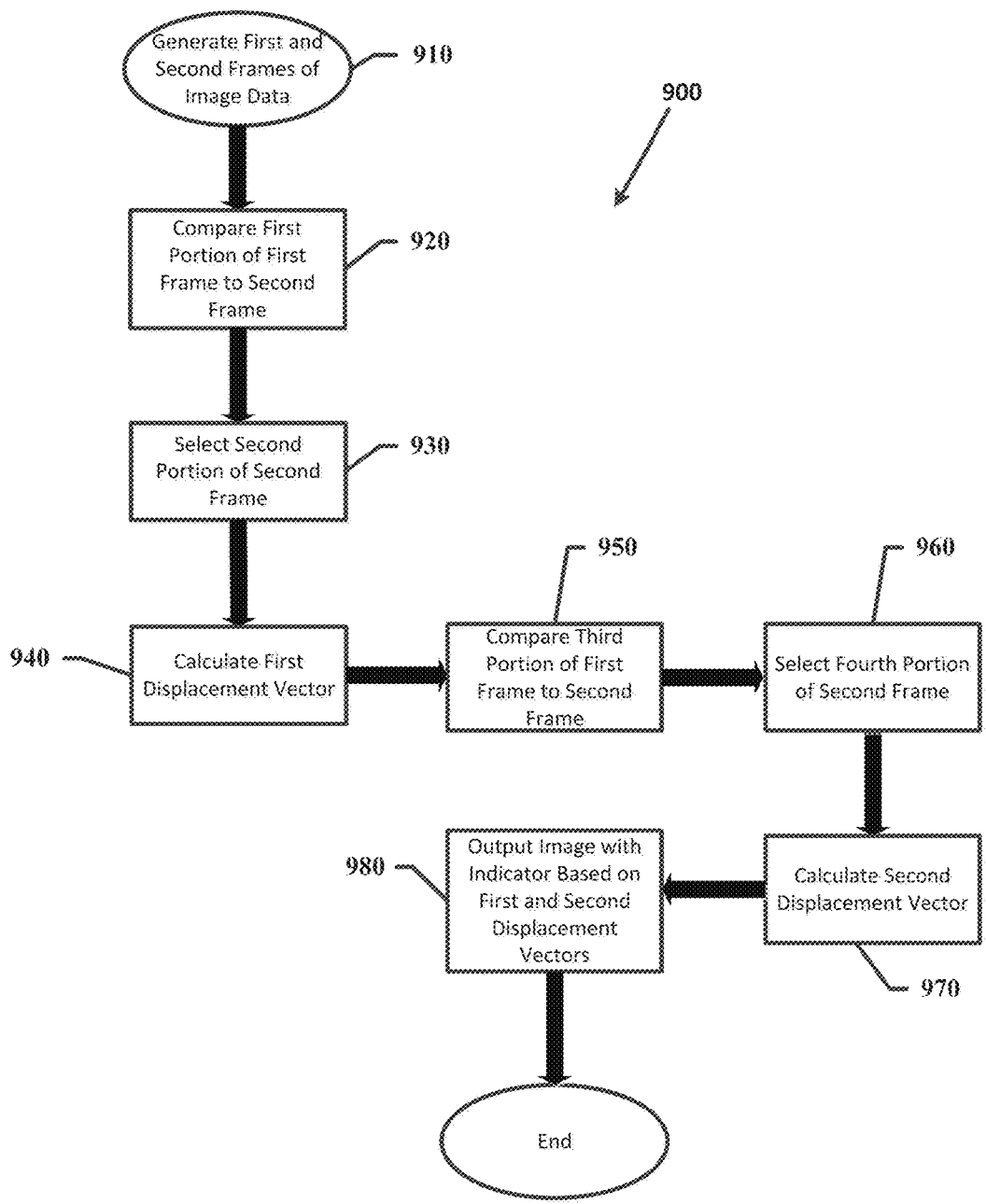
FIG. 9 is a flow diagram illustrating an embodiment of a method for segmenting an image.

FIG. 9 shows a flow diagram of an embodiment of a method 900 for segmenting an image. The method 900 includes generating first and second frames of image data (step 910). This step can include acquiring a plurality of data vectors at a first time to form a first frame of image data, and acquiring a plurality of data vectors at a second, different time to form the second frame of image data. Data vectors can be acquired in some examples using an intravascular imaging system having an intravascular imaging device (e.g., ultrasound transducer) for emitting and receiving acoustic energy at the imaging device similar to that described previously.

The embodiment of the method 900 further includes selecting a first portion of the first frame having a subset of the image data of the first frame, and comparing the first portion to image data of the second frame (step 920). In some examples, this step can include comparing the first portion to all image data of the second frame. In other examples, this step can include comparing the first portion to a subset of the image data of the second frame, such as comparing the first portion only to image data within a search window of the second frame.

As illustrated, the embodiment of the method 900 also includes selecting a second portion having a subset of image data of the second frame based on the comparison of the first portion of the first frame to image data of the second frame (step 930). The second portion of the second frame can be selected based on the comparison by determining that the subset of image data represented by the second portion corresponds to the subset of image data represented by the first portion. The image data of the second portion may correspond to the image data of the first portion where the image data of the second portion corresponds to the image data of the first portion to a greater degree than image data of any other portion of the second frame. In one example, the second portion can be selected as the portion of the second frame that has a lowest numerical matching error with the image data represented by the first portion.

Using the selected first portion of the first frame and the selected second portion of the second frame, the method 900 additionally includes calculation of a first displacement vector (step 940). The first displacement vector (e.g., a length of the first displacement vector) can represent relative movement between the selected first portion and the selected second portion over a period of time between the generation of the first and second frames. Therefore, the first displacement vector can represent relative movement of the image data represented by the corresponding first and second portions of the respective first and second frames over the period of time.

The embodiment of the method 900 further includes selecting a third portion of the first frame having a subset of the image data of the first frame, and comparing the third portion to image data of the second frame (step 950). The third portion of the first frame can be a different portion than the first portion of the first frame, and thus may represent different image data of the first frame than the first portion. This step can be similar to the comparison of the first portion to image data of the second frame as described previously.

A fourth portion having a subset of image data of the second frame is selected based on the comparison of the third portion of the first frame to image data of the second frame (step 960). This step can be similar to the selection of the second portion of the second frame as described previously.

Using the selected third portion of the first frame and the selected fourth portion of the second frame, the method 900 additionally includes calculation of a second displacement vector (step 970). The second displacement vector (e.g., a length of the second displacement vector) can represent relative movement between the selected third portion and the selected fourth portion over a period of time between the generation of the first and second frames. Therefore, the second displacement vector can represent relative movement of the image data represented by the corresponding third and fourth portions of the respective first and second frames over the period of time.

The embodiment of the method 900 may further include outputting an image with an indicator thereon, where the location of the indicator on the image is determined by using the calculated first and second displacement vectors (step 980). This step may include comparing the first and second displacement vectors, such as comparing a length of the first displacement vector to a length of the second displacement vector. It may be determined that respective image data of the first and third portions of the first frame represents differing items in an imaging view where the length of first displacement vector differs from the length of the second displacement vector beyond a predetermined degree.

By using the comparison of first and second displacement vectors to distinguish different items in an imaging view, an image can be output with an indicator showing the different items in the imaging view. In one such example, the indicator can show an interface between different items in the imaging view. As a result, the generated image with the indicator may be useful in diagnostic procedures where a geometry of a vessel plays a role in the diagnosis and the determination for a need to take interventional actions with respect to the vessel.

Embodiments also include systems that perform the described method. For example, a further embodiment can include an imaging system. The system may include a catheter assembly with an intravascular imaging device (e.g., including an ultrasound transducer) to generate imaging data. The image data generated by the catheter assembly can represent a plurality of image elements. The system may also include a user interface having an image display region. In some examples, the user interface can be configured to receive inputs from a user, and may include, at least in part, one or more touchscreens. The system can further include an imaging engine in communication with the intravascular imaging device and the user interface.

The imaging engine may have at least one processor that can be used in segmenting an image to be displayed on the user interface. The imaging engine can be configured to receive a plurality of data vectors forming a first frame of image data and a plurality of data vectors forming a second frame of image data. In some cases, the respective data vectors forming the first frame can be taken over a first period of time, and the plurality of data vectors forming the second frame can be taken over a second period of time different from the first period of time (e.g., previous to or subsequent to the first period of time). In one example, a patient's heart rate can be used as an input to the imaging engine for generating the first and second frames at desired portions a patient's cardiac cycle. Using the at least one processor, the imaging engine can compare a portion of the first frame to image data of the second frame. Based on the comparison, using the at least one processor the imaging engine can select a portion of the image data of the second frame corresponding to the portion of the first frame. A displacement vector representing movement over the period of time of the corresponding image data in the portions of the first and second frames can then be calculated by the imaging engine using the at least one processor. This process can be repeated to calculate a number of displacement vectors for different portions of the image data. The imaging engine, using the at least one processor, can compare the displacement vectors to identify differential movement of items represented by the image data. This can include the at least one processor comparing relative lengths of the displacement vectors. Finally, the at least one processor can determine a location on the displayed image for an indicator using the comparison of the displacement vectors.

Another embodiment can include a non-transitory computer-readable storage article having computer-executable instructions sorted thereon to cause at least one programmable processor to display an image having an indicator for one or more items in the imaging view. The at least one programmable processor may receive a plurality of data vectors forming first and second data frames corresponding to different times. The at least one programmable processor can compare a portion of the first frame to image data of the second frame. Based on the comparison, the at least one programmable processor can select a portion of the image data of the second frame corresponding to the image data of the portion of the first frame. A displacement vector representing movement over the period of time of the corresponding image data in the portions of the first and second frames can then be calculated by the at least one programmable processor. This process can be repeated to calculate a number of displacement vectors for different portions of the image data. The at least one programmable processor can compare the displacement vectors to identify differential movement of items represented by the image data. This can include the at least one programmable processor comparing relative lengths of the displacement vectors. Finally, the at least one programmable processor can determine a location on the displayed image for an indicator using the comparison of the displacement vectors.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

The invention claimed is:

1. A method of segmenting an image, the method comprising the steps of:
generating a first frame of image data representing a plurality of items in an imaging view at a first time;
generating a second frame of image data representing a plurality of items in an imaging view at a second time, the second time differing from the first time;
selecting a first portion of the first frame, the first portion having a first subset of the image data of the first frame;
comparing the selected first portion to image data of the second frame;
selecting a second portion of the second frame based on the comparison, the second portion having a second subset of the image data of the second frame;
calculating a first displacement vector representing relative movement between the first portion at the first time and the second portion at the second time;
selecting a third portion of the first frame, the third portion having a third subset of the image data of the first frame, and wherein the third subset of the image data of the first frame differs from the first subset of the image data of the first frame;
comparing the selected third portion to image data of the second frame;
selecting a fourth portion of the second frame based on the comparison, the fourth portion having a fourth subset of the image data of the second frame;
calculating a second displacement vector representing relative movement between the third portion at the first time and the fourth portion at the second time;
comparing a length of the first displacement vector to a length of the second displacement vector; and
based on the length of the first displacement vector differing from the length of the second displacement vector, determining that the first portion of the first frame of image data represents blood within a vessel and the third portion of the first frame of image data represents vessel tissue or plaque.

2. The method of claim 1, wherein the second portion is selected based on the comparison by determining that the second subset of image data corresponds to the first subset of image data to a greater degree than image data of any other portion of the second frame.

3. The method of claim 2, wherein comparing the selected first portion to image data of the second frame comprises calculating a matching error between the first subset of image data of the selected first portion and each of a plurality of portions having a subset of image data of the second frame.

4. The method of claim 3, wherein selecting the second portion of the second frame based on the comparison comprises selecting as the second portion one of the plurality of portions of the second frame that has the lowest calculated matching error with the selected first portion.

5. The method of claim 2, wherein comparing the selected first portion to image data of the second frame comprises comparing the selected first portion to image data of the second frame that is part of a search window of the second frame, the search window comprising a subset of all image data of the second frame.

6. The method of claim 5, wherein the search window is larger than the selected first and second portions, and wherein the second portion is selected based on the comparison by determining that the second subset of image data corresponds to the first subset of image data to a greater degree than image data at any other portion of the search window of the second frame.

7. The method of claim 5, wherein the search window comprises the subset of all image data of the second frame excluding image data of the second frame forming a perimeter of the second frame.

8. The method of claim 1, further comprising the steps of:
outputting on the display an image having an indicator at a location on the image that represents an interface between blood within the vessel and vessel tissue or plaque.

9. The method of claim 8, wherein the fourth portion is selected based on the comparison by determining that the fourth subset of image data corresponds to the third subset of image data to a greater degree than image data of any other portion of the second frame.

10. The method of claim 8, further comprising the step of:
determining that the first portion of the first frame of image data represents blood within a vessel and the third portion of the first frame of image data represents vessel tissue or plaque based on the length of the first displacement vector differing from the length of the second displacement vector beyond a predetermined degree.

11. The method of claim 1, wherein the first time corresponds to a first part of a cardiac cycle and the second time corresponds to a second part of the cardiac cycle that is different from the first part of the cardiac cycle.

12. The method of claim 11, wherein the first frame of image data and the second frame of image data are generated using an intravascular ultrasound imaging system, and wherein using the intravascular ultrasound imaging system comprises collecting cross-sectional image data using a catheter assembly that includes an intravascular imaging device having an imaging module for emitting and receiving energy.

13. The method of claim 1, further comprising the step of:
measuring a heart rate of a patient, wherein the first and second times are determined using the measured heart rate of the patient.

14. The method of claim 13, wherein the measured heart rate of the patient is used to determine the first time and the second time as corresponding to a same part of a cardiac cycle.

15. An imaging system comprising:
a catheter assembly including an intravascular imaging device having an imaging module configured to emit and receive energy at a first time to generate a first frame of image data and emit and receive energy at a second time that is different from the first time to generate a second frame of image data, wherein the image data represents a plurality of image elements;
a user interface including an image display region; and
an imaging engine in communication with the intravascular imaging device and the user interface and comprising at least one processor, the imaging engine being configured to:
select, using the at least one processor, a first portion of the first frame, the first portion having a first subset of the image data of the first frame;
compare, using the at least one processor, the selected first portion to image data of the second frame;
select, using the at least one processor, a second portion of the second frame based on the comparison, the second portion having a second subset of the image data of the second frame;
calculate, using the at least one processor, a first displacement vector representing relative movement between the first portion at the first time and the second portion at the second time;
select, using the at least one processor, a third portion of the first frame, the third portion having a third subset of the image data of the first frame, and wherein the third subset of the image data of the first frame differs from the first subset of the image data of the first frame;
compare, using the at least one processor, the selected third portion to image data of the second frame;
select, using the at least one processor, a fourth portion of the second frame based on the comparison, the fourth portion having a fourth subset of the image data of the second frame;
calculate, using the at least one processor, a second displacement vector representing relative movement between the third portion at the first time and the fourth portion at the second time;
compare a length of the first displacement vector to a length of the second displacement vector; and
based on the length of the first displacement vector differing from the length of the second displacement vector, determine that the first portion of the first frame of image data represents blood within a vessel lumen and the third portion of the first frame of image data represents vessel tissue or plaque.

16. The system of claim 15, wherein the imaging engine is further configured to:
output on the image display region an image having an indicator representing an interface between blood within the vessel lumen and vessel tissue or plaque.

17. The system of claim 16, wherein the second portion is selected based on the comparison by determining that the second subset of image data corresponds to the first subset of image data to a greater degree than image data of any other portion of the second frame, and wherein the fourth portion is selected based on the comparison by determining that the fourth subset of image data corresponds to the third subset of image data to a greater degree than image data of any other portion of the second frame.

18. The system of claim 17, wherein the imaging engine is further configured to:
determine that the first portion of the first frame of image data represents blood within a vessel lumen and the third portion of the first frame of image data represents vessel tissue or plaque based on the length of the first displacement vector differing from the length of the second displacement vector beyond a predetermined degree.

19. A non-transitory computer-readable storage article having computer-executable instructions stored thereon to cause at least one programmable processor to:
select a first portion of a first frame of image data, the first frame of image data representing a plurality of image elements generated at a first time, the first portion having a first subset of the image data of the first frame;
compare the selected first portion to image data of a second frame of image data, the second frame of image data representing a plurality of image elements generated at a second time;
select a second portion of the second frame based on the comparison, the second portion having a second subset of the image data of the second frame;
calculate a first displacement vector representing relative movement between the first portion at the first time and the second portion at the second time;
select a third portion of the first frame of image data, the third portion having a third subset of the image data of the first frame, and wherein the third subset of the image data of the first frame differs from the first subset of the image data of the first frame;
compare the selected third portion to image data of the second frame;
select a fourth portion of the second frame based on the comparison, the fourth portion having a fourth subset of the image data of the second frame;
calculate a second displacement vector representing relative movement between the third portion at the first time and the fourth portion at the second time;
compare a length of the first displacement vector to a length of the second displacement vector;
based on the length of the first displacement vector differing from the length of the second displacement vector, determine that the first portion of the first frame of image data represents blood within a vessel lumen and the third portion of the first frame of image data represents vessel tissue or plaque; and
position an indicator on an image at a location representing an interface between blood within the vessel lumen and vessel tissue or plaque.

20. The article of claim 19, wherein the first portion of the first frame of image data is determined to represent blood within the vessel lumen and the third portion of the first frame of image data is determined to represent vessel tissue or plaque based on the length of the first displacement vector differing from the length of the second displacement vector beyond a predetermined degree.

* * * * *